United States Patent [19]

Meisch et al.

[11] 4,443,219

[45] Apr. 17, 1984

[54] SYSTEM FOR ASEPTICALLY DRAINING A URINE BAG

[75] Inventors: Charles E. Meisch, Hasbrouck Heights; David M. Keating, Landing, both of N.J.

[73] Assignee: C. R. Bard, Inc., Murray Hill, N.J.

[21] Appl. No.: 242,272

[22] Filed: Mar. 10, 1981

[51] Int. Cl.$^3$ .............................................. A61M 1/00
[52] U.S. Cl. .................................. 604/317; 604/323; 604/256; 604/410
[58] Field of Search ............... 128/DIG. 24, DIG. 28, 128/227, 295, 274, 275, 272, 272.1, 272.3, 275; 141/313, 314, 317, 318, 344, 345, 346, 347, 348, 349; 222/83, 83.5; 251/149.1, 149.2; 150/9; 604/322, 323, 325, 326, 350, 410, 249, 256 (U.S. only)

[56] References Cited

U.S. PATENT DOCUMENTS

| | | | |
|---|---|---|---|
| 584,091 | 6/1897 | Leidich | 251/149.2 |
| 756,582 | 4/1904 | Chaplin | 251/149.2 |
| 3,415,299 | 12/1968 | Hinman, Jr. | 128/275 |
| 3,486,730 | 12/1969 | Potash | 141/346 |
| 3,529,599 | 9/1970 | Folkman et al. | 604/323 |
| 3,838,691 | 10/1974 | Paludin | 128/275 |
| 3,888,126 | 6/1975 | Cross | 604/323 |
| 4,143,853 | 3/1979 | Abramson | 251/149.1 |
| 4,280,498 | 7/1981 | Jensen | 128/283 |
| 4,319,573 | 3/1982 | Whitlock | 128/275 |

Primary Examiner—C. Fred Rosenbaum
Assistant Examiner—J. L. Kruter
Attorney, Agent, or Firm—Dennison, Meserole, Pollack & Scheiner

[57] ABSTRACT

A system for aseptically removing urine from a primary drainage bag attached to a patient by conventional catheter means which includes a separate sterile disposable transfer bag. Rigid laterally extending spout interconnects the two bags when drainage is desired. The primary drainage bag is formed in the preferred embodiment with an outlet provided with self-closing flaps and slip valves which may be penetrated by the spout mounted on the transfer bag. Locking rib and groove means secure the spout in the outlet and a removable cap covers the outlet when the transfer bag is not attached. In a second form, the spout and valve means are on the primary drainage bag and transfer bag respectively.

5 Claims, 6 Drawing Figures

SYSTEM FOR ASEPTICALLY DRAINING A URINE BAG

BACKGROUND OF THE INVENTION

This invention relates generally to closed system urinary drainage bags of the type conventionally used in hospitals and health care facilities when it is necessary to collect urine from a patient over an extended period of time. Such bags are routinely used by post-operative patients as well as those with urological disorders for collection, measuring and frequently testing of the urinary output. In use, the patient is first catheterized and the catheter is then connected to the drainage bag through a length of tubing. The bag is normally supported below the patient's level, either from the bed rail or other support, and the urine drains by gravity from the patient through the catheter, the tubing, and then finally into the bag. Almost all such bags are provided with drain ports through which measured quantities of urine may be removed from time to time for various testing procedures. More particularly, the instant invention herein relates to a new system for aseptically draining urine from the primary urine bag into a separate sterile disposable transfer bag.

A typical urine drainage bag known in the prior art is shown in the copending application of Charles E. Meisch et al, Ser. No. 116,625, filed Jan. 29, 1980 now U.S. Pat. No. 4,312,352.

One of the drawbacks with prior art bags is the possibility of contamination and infection to the patient when the bags are opened for removal of all or part of the contents thereof. During such opening, air is permitted to enter into the outlet spout and bacteria can then migrate up the spout into the bag and finally up through the connecting tubing and the catheter into the bladder thereby causing infection. Additionally, there is the problem of contamination of hospital personnel due to splattering of urine during the collection process.

The principal advantage of the present system over the known prior art is the provision for the first time of aseptically draining urine from the principal bag into an auxiliary drainage bag which is sterile and disposable, thereby obviating problems of infection.

SUMMARY AND OBJECTS OF THE INVENTION

A urine drainage bag is provided with a specially constructed outlet including a valved closure affixed to the lower portion of the bag which may be completely sealed by a removable cap. A secondary sterile disposable urine transfer bag is provided with a means for aseptically connecting with said valved closure to allow drainage of the contents of the first bag into the transfer bag. An example of such a means is a penetrating spout assembly mounted on either bag, said spout adapted to be inserted into the outlet of the other bag, thus opening the valve mechanism and permitting transfer of fluid from the principal bag into the transfer bag.

It is a primary object of the present invention to provide a simple, safe and sterile transfer system for removing urine from a primary drainage bag into a secondary transfer bag.

It is a further object of this invention to provide an interconnection between a primary urine collection bag and a transfer bag that automatically establishes flow between the bags when the connection is engaged.

A further object of the invention is to provide a sterile and completely sealed outlet opening in a urine bag which may be penetrated by a specially formed spout attached to a secondary urine transfer bag, and which connection can be effected without risk of contamination of either the patient or the medical personnel.

A further object of the invention is to provide a system for aseptically draining a urine bag which may be easily and inexpensively manufactured from plastic materials and is safe and convenient in use.

Various other objects and advantages of our invention will be readily apparent from the following detailed description taken in conjunction with the drawings in which an exemplary embodiment of the invention is shown.

DESCRIPTION OF A PREFERRED EMBODIMENT

Figure 1:
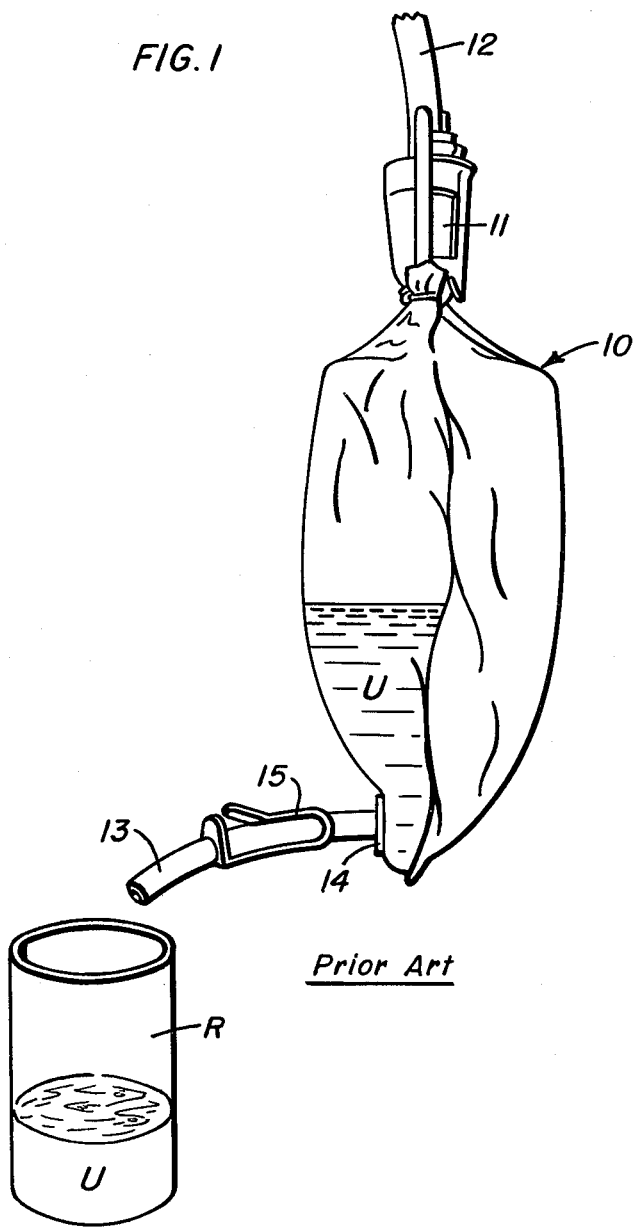
FIG. 1 is a perspective showing of a typical prior art urine drainage bag showing removal of the contents into a receptacle.

Referring now to the drawings, a conventional urine drainage bag is shown in FIG. 1 at 10 which bag is conventionally formed by peripheraly heat sealing or otherwise securing a pair of flat vinyl or polyvinyl chloride sheets together. The bag is provided with an inlet opening adjacent the top for reception of a drip chamber 11 which may also have integral therewith a bacterial air filter. The drip chamber is connected to a tube 12 which in turn is connected at its end, not shown, to a conventional Foley catheter or the like which is in turn inserted in the urethral canal of the patient.

Bag 10 is also provided with an outlet hose or drainage tube 13 which may be permanently secured to the bag by heat sealing a flange member 14 thereon. A spring metal pinch clamp 15 is provided on the tubing 13 for the purpose of opening and closing the passage through the tube. As shown in FIG. 1, a receptacle R may be placed beneath the end of tube 13 and will receive urine U from the tube and the bag 10 when the pinch clamp 15 is open as shown. When the clamp is in the closed position, the free end of tube 13 is conventionally received in a housing which is sealed to the face of the bag. This is no part of the instant invention but may be noted in the copending application noted above.

Figure 2:
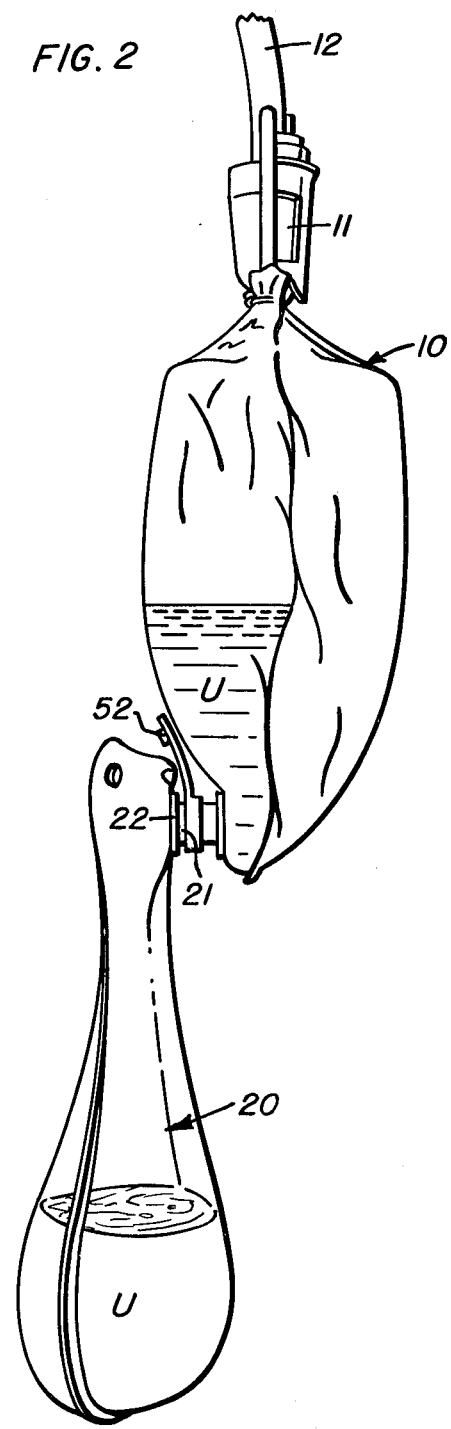
FIG. 2 is a similar perspective view showing our new invention with the two bags interconnected.

The system for aseptically draining urine that constitutes the present invention is shown in FIG. 2 and includes a bag 10 virtually the same as the bag in the prior art also utilizing the drip chamber 11 and the tube 12. Here it will be seen however that the outlet port and flange assembly 13, 14, and 15, has been replaced by a specific outlet construction shown in FIGS. 3-6. A sterile disposable transfer bag 20 is provided to receive urine from the primary drainage bag 10. The transfer bag may be formed in a similar manner and from materials similar to that of the principal bag but is totally closed at the top and has provided adjacent the upper wall thereof an inlet opening provided with an outwardly extending spout 21. The spout may be secured to the bag 20 by welding of a flange 22 will as is common in the art. The distal end of the spout is straight as shown at 23 and spaced rearwardly from the tip is a wide shoulder 24 which serves as an abutment as later described. There is a gradual curve 25 extending from the spout shaft to the shoulder. This curved surface seats against the outer face of a slit valve as will appear further herein. An annular groove 26 circumscribes the spout wide portion rearwardly of shoulder 24 and acts in conjunction with a circular rib on the main bag outlet to lock the spout therein. A circular abutment flange 27 at the rear of the wide portion further limits penetration of the spout into the outlet as shown in FIG. 1. An axial bore 28 extends throughout the spout for conveying the urine between the two bags.

Primary urine drainage bag 10 is formed with a circular opening 30 adjacent the lower end of its outer face. A capped outlet assembly 31 is attached directly over this opening and consists of a plastic housing 32 having a peripheral mounting flange 33 at one end which may be chemically or thermally welded to the bag face. The opposite end of the housing 32 has an annular lip 34 formed thereon on the exterior barrel. Interiorly of the housing and adjacent the mounting flange 33, a flap valve abutment 35 is formed.

Figure 3:
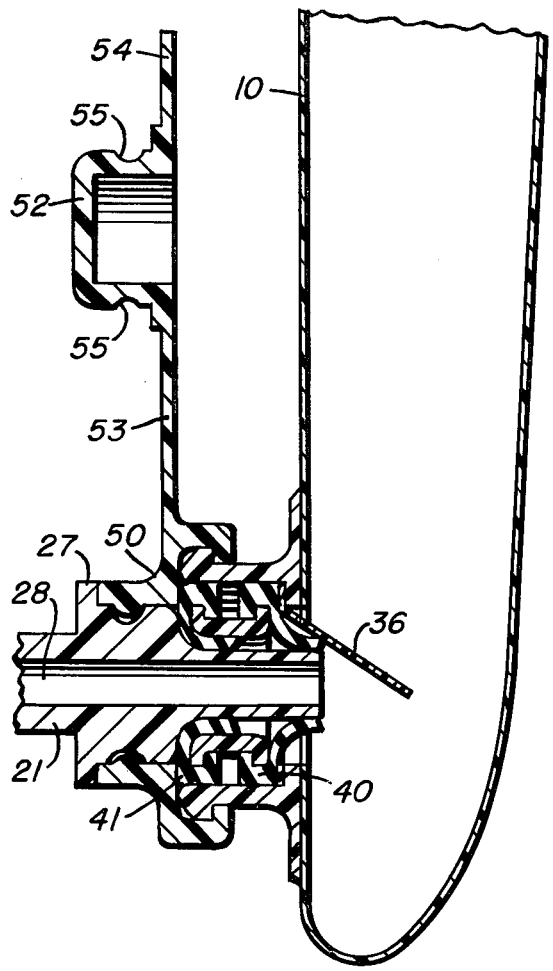
FIG. 3 is a vertical section through the primary drainage bag and showing the interconnection of the transfer bag spout thereto.
Figure 4:
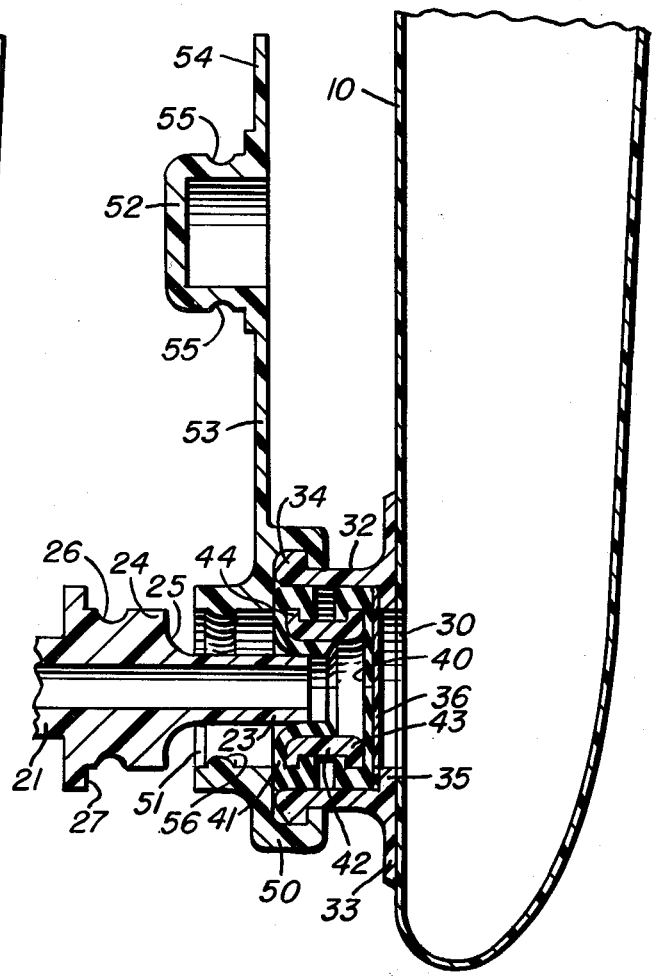
FIG. 4 is a sectional view similar to FIG. 3 but prior to full engagement of the spout.

A thin circular flap valve 36 engages against the abutment 35 and is basically a nearly full circle cut into a flat circular disc so that it can be displaced inwardly as shown in FIG. 3. A pair of identical slit valves 40 and 41 are mounted internally of the housing barrel by a mounting collar 42. This collar has peripheral flanges 43 and 44 which engage behind inwardly turned flanges 45 and 46 on the slit valve assemblies. The face of the slit valves 47 are slit as at 48 in FIG. 6 to provide a plurality of fingers. While three such fingers are shown, it is to be understood that this is merely exemplary and any number could be employed. Since the face 47 is formed of an elastomeric material, the slits 48 will seal when the valve is undisturbed as in FIGS. 5 and 6 and will block fluid passage. Note that slit valve 40 seals face to face against the flap valve 36 as in FIG. 4.

A cover assembly for the outlet is provided at 50 and has an opening 51 into which spout 21 may be inserted. The cover assembly has an internal annular recess receiving the annular lip 34 on the barrel and is retained thereon in a snap fit. A cap 52 is tethered to cover assembly 50 by an integrally formed retainer strap 53. A thumb tap 54 extends opposite the strap for ease in applying and removing the cap.

Figure 5:
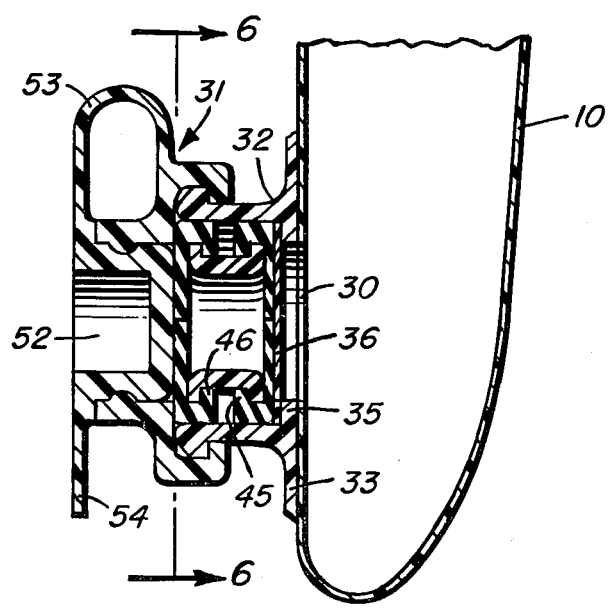
FIG. 5 is a sectional view of the lower portion of the primary urine drainage bag showing the outlet and valve assembly closed by the cap.
Figure 6:
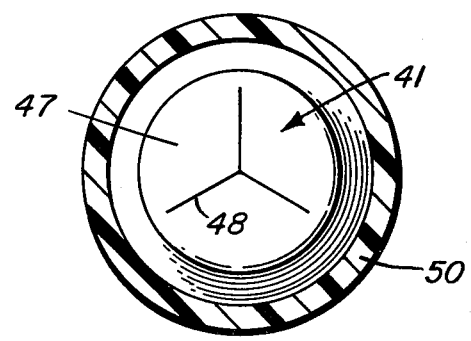
FIG. 6 is a sectional view taken along the lines 6—6 of FIG. 5 and specifically showing the slit valve face.

Cap 52 is annularly grooved as at 55 to cooperate as shown in FIG. 5 with ridge 56 formed interiorly of the cover assembly. The ridge also cooperates in the same manner with groove 26 of the spout to ensure a snap fit sealed connection.

It will be understood that cap 52 can be made as a separate piece rather than formed integrally with the cover assembly shown in the preferred embodiment shown.

OPERATION

In use, the primary urine drainage bag is connected to the patient via a Foley catheter in the conventional manner and supported from a hanger or the like at a level below that of the patient. During this procedure and while the bag is in use, the cap 52 is in place covering the outlet as shown in FIG. 5. Here the flap valve 36 and slit valves 40 and 41 prevent urine from passing through the outlet. To empty the system without exposing it to the bacteria in the air, cap 52 is removed from the outlet and the outer face of slit valve 41 is cleaned with a suitable solution. Urine removal into the bag 20 is accomplished by inserting the spout 21 of the secondary drainage bag through the two slit valves 40 and 41 and displacing flap valve 36 as in FIGS. 3 and 4. Spout 21 is inserted until it locks into position with abutment flange 27 engaging the face of cover assembly 50 and groove 26 engaging rib 56.

This will then allow transfer of the urine from the primary bag into the secondary bag. Flow will immediately cease upon removal of spout 21 as the slit valves and flap valve will automatically close.

During the transfer process all air replacing urine in the primary drainage bag 10 will pass through the bacterial filter keeping the bag interior free from contamination.

In the alternative, a valved spout could be mounted on the primary bag. The transfer bag would then have a valved opening which would cooperate with the valved spout so that mating of the primary bag spout with the opening in the transfer bag would cause the valve to open, thus effecting drainage of said primary bag.

It must be recognized that the above is descriptive of two embodiments for effecting sterile drainage of the contents of a valved drainage bag into a second transfer container without causing the interior of the drainage bag to become nonsterile. The specific structural features of the two bags can be varied within the scope of the basic concept and the product or its method of use is not limited to the embodiments disclosed above.

We claim:

1. A system for aseptically removing urine from a drainage bag connected to a catheterized patient, said system comprising an outlet on said drainage bag adjacent the bottom thereof, normally closed valve means operatively connected to said outlet preventing flow therethrough, a housing means having an end face secured thereto and around said outlet, said valve means including a thin resilient wall having inner and outer faces and extending across the interior of the housing means and being centrally slit to form a self-closing slit valve, a second slit valve within the housing means spaced outwardly of said first slit valve, a flap closure within the housing means and being normally closed and resting against the inner face of said first mentioned slit valve, and a transfer bag for receiving urine removed from said drainage bag, spout means on said transfer bag, means on said transfer bag adapted to mate with said housing means of the drainage bag, said spout means adapted when inserted in said outlet to open both of said slit valves and flap closure to initiate removal of urine from said drainage bag.

2. A system as defined in claim 1 and further including removable cap means for sealing the end of said housing means when said transfer bag is not in use.

3. A system as defined in claim 1 wherein said spout means has a limit stop abutment thereon adapted to contact the end face of said housing means.

4. A system as defined in claim 1 wherein the means on the transfer bag adapted to mate with the housing means comprises cooperating lock means on said spout and on said housing means for securing the bags in the urine transfer position.

5. A system as defined in claim 4 wherein the lock means comprises an annular ridge formed on one of said spout and housing means and an annular ridge receiving groove formed on the other, at least said housing means being formed of resilient plastic material.

* * * * *